United States Patent [19]

Sachse et al.

[11] Patent Number: 6,008,928
[45] Date of Patent: Dec. 28, 1999

[54] MULTI-GAS SENSOR

[75] Inventors: Glenn W. Sachse, Yorktown, Va.;
Liang-guo Wang, Milpitas, Calif.;
Peter J. LeBel, Newport News, Va.;
Tommy C. Steele, Yorktown, Va.;
Mauro Rana, Hampton, Va.

[73] Assignee: The United States as represented by the Administrator of the National Aeronautics and Space Administration, Washington, D.C.

[21] Appl. No.: 09/019,473

[22] Filed: Feb. 5, 1998

Related U.S. Application Data

[60] Provisional application No. 60/067,917, Dec. 8, 1997, and provisional application No. 60/073,822, Feb. 5, 1998.

[51] Int. Cl.$^6$ ..................................................... G02F 1/03
[52] U.S. Cl. .......................... 359/246; 359/247; 359/281; 359/252; 356/437; 250/338.5
[58] Field of Search ..................................... 359/246, 247, 359/281, 252, 287, 250; 250/338.5, 338.1, 339.13; 356/437, 438, 346, 414

[56] References Cited

U.S. PATENT DOCUMENTS

| | | | |
|---|---|---|---|
| 4,489,239 | 12/1994 | Grant et al. | 250/339.03 |
| 4,507,558 | 3/1985 | Bonne . | |
| 4,567,366 | 1/1986 | Shinohara . | |
| 4,841,149 | 6/1989 | Martin et al. . | |
| 4,924,095 | 5/1990 | Swanson, Jr. et al. | 250/338.5 |
| 4,963,742 | 10/1990 | Abernathy . | |
| 4,999,498 | 3/1991 | Hunt et al. | 250/338.5 |
| 5,076,699 | 12/1991 | Ryan et al. | 356/437 |
| 5,117,676 | 6/1992 | Chang | 73/40.5 A |
| 5,128,797 | 7/1992 | Sachse et al. | 359/246 |
| 5,134,361 | 7/1992 | Pillow | 359/247 |
| 5,162,944 | 11/1992 | Yamamoto et al. | 359/247 |
| 5,210,702 | 5/1993 | Bishop et al. | 250/338.5 |
| 5,252,828 | 10/1993 | Kert et al. | 250/339.13 |
| 5,306,913 | 4/1994 | Noack et al. | 250/338.5 |
| 5,319,199 | 6/1994 | Stedman et al. | 250/338.5 |
| 5,343,043 | 8/1994 | Johnson et al. | 250/338.5 |
| 5,343,736 | 9/1994 | Cady et al. | 73/40 |
| 5,371,367 | 12/1994 | DiDomenico et al. | 250/338.5 |
| 5,401,967 | 3/1995 | Stedman et al. | 250/338.5 |
| 5,721,632 | 2/1998 | Billmers et al. | 359/252 |

OTHER PUBLICATIONS

D. E. Burch and J.D. Penbrook, "Instrument to monitor $CH_4$, CO, and $CO_2$ in auto exhaust," Environmental Protection Agency, Washington, DC, EPA Rep. 650/2–73–030, Oct. 1973.

*Primary Examiner*—Loha Ben
*Attorney, Agent, or Firm*—Robin W. Edwards

[57] ABSTRACT

A multi-gas sensor is provided which modulates a polarized light beam over a broadband of wavelengths between two alternating orthogonal polarization components. The two orthogonal polarization components of the polarization modulated beam are directed along two distinct optical paths. At least one optical path contains one or more spectral discrimination element, with each spectral discrimination element having spectral absorption features of one or more gases of interest being measured. The two optical paths then intersect, and one orthogonal component of the intersected components is transmitted and the other orthogonal component is reflected. The combined polarization modulated beam is partitioned into one or more smaller spectral regions of interest where one or more gases of interest has an absorption band. The difference in intensity between the two orthogonal polarization components is then determined in each partitioned spectral region of interest as an indication of the spectral emission/absorption of the light beam by the gases of interest in the measurement path. The spectral emission/absorption is indicative of the concentration of the one or more gases of interest in the measurement path. More specifically, one embodiment of the present invention is a gas filter correlation radiometer which comprises a polarizer, a polarization modulator, a polarization beam splitter, a beam combiner, wavelength partitioning element, and detection element. The gases of interest are measured simultaneously and, further, can be measured independently or non-independently. Furthermore, optical or electronic element are provided to balance optical intensities between the two optical paths.

29 Claims, 11 Drawing Sheets

MULTI-GAS SENSOR

CLAIM OF BENEFIT OF PROVISIONAL APPLICATIONS

Pursuant to 35 U.S.C. Section 119, the benefit of priority from provisional application Ser. No. 60/067,917, with a filing date of Dec. 8, 1997 and provisional application serial number 60/073,822, with a filing date of Feb. 5, 1998, is claimed for this non-provisional application.

ORIGIN OF THE INVENTION

The invention described herein was jointly made by employees of the United States Government and during the performance of work under NASA contracts and is subject to provisions of Section 305 of the National Aeronautics and Space Act of 1958, as amended, Public Law 85-568 (72 Stat. 435; 42 USC 2457), and 35 USC 202, respectively. In accordance with 35 USC 202, the contractor elected not to retain title.

BACKGROUND OF THE INVENTION

1. Technical Field of the Invention

The present invention relates to the simultaneous measurement of two or more gases using optical path switching. More specifically, it relates to such measurement using dual beam spectroscopy, including gas filter correlation radiometry.

2. Discussion of the Related Art

Optical path switching has many potential applications, particularly in the field of dual beam spectroscopy. In dual beam spectroscopy, light from a radiation source traverses a measurement path and is then divided between two optical paths. Each optical path generally contains some medium through which the radiation is transmitted and thus partially absorbed and/or reflected. The key measurement in this type of spectroscopy is related to the intensity difference of the radiation that takes these two paths. For illustrative purposes, a gas filter correlation radiometer (GFCR), one example of a dual beam spectrometer, will be discussed in detail.

Gas filter correlation radiometers (GFCRs) may infer the concentration of a gas species along some measurement path either external or internal to the GFCR. In many GFCRs, gas sensing is accomplished by viewing alternately through two optical cells the emission/absorption of the gas molecules along the measurement path. These two optical cells, often called the correlation and vacuum cells, are an example of the media found in the two optical paths of a dual beam spectrometer. The correlation cell contains a high optical depth of gas species i and thus strongly absorbs radiation at the molecular transition wavelengths of the particular gas. In effect, the correlation cell acts as a spectral "notch filter" to the incoming radiation, the spectral notches being coincident with the band structure of gas species i. The vacuum cell generally encloses a vacuum or a gas or gas mixture exhibiting negligible or no optical depth, e.g., nitrogen, an inert gas, or even clean dry air. The difference in signal between these two views of the emitting/absorbing gas species i within the spectral region of interest plus, or in combination with, the sum of the signals of these two views can be related to the concentration of this gas along the measurement path.

In one known GFCR for measuring a single gas concentration in a particular quantity disclosed in U.S. Pat. No. 5,128,797, issued to Sachse et al. and assigned to the National Aeronautics and Space Administration (NASA), the specification of which is hereby incorporated by reference, a non-mechanical optical path switch comprises a polarizer, polarization modulator and a polarization beam splitter. The polarizer polarizes light from a light source into a single, e.g., vertically polarized, component which is then rapidly modulated into alternate vertically and horizontally polarized components by a polarization modulator. The polarization modulator may be used in conjunction with an optical waveplate. The polarization modulated beam is then incident on a polarization beam splitter which transmits light of one orthogonal component, e.g., horizontally polarized, and reflects light of a perpendicular component, e.g., vertically polarized. In a gas filter correlation radiometer application, the transmitted horizontally polarized beam is reflected by a mirror, passes through a gas correlation cell, and is transmitted through a second beam splitter. The reflected vertically polarized beam passes through a vacuum cell, is reflected by a mirror and then reflected by the second beam splitter. The beam combiner recombines the horizontal and vertical components into a single beam which is read by a conventional detector. This approach has numerous advantages, such as no mechanical means being required to alternate the view of the detector through the correlation and vacuum cells, fast response, etc.

It would be desirable, in numerous applications, to be able to measure two or more gas concentrations simultaneously, either independently or non-independently, with a single device using an optical path switch. It further would be desirable to do such measurement with optimal optical balance.

OBJECTS OF THE INVENTION

It is accordingly an object of the present invention to provide a device to simultaneously, but not independently, measure two or more gases of interest.

It is another object of the present invention to provide a device to simultaneously, but not independently, measure two or more gases of interest with negligible or no spectral interference.

It is another object of the present invention to provide a device to simultaneously and independently measure two or more gases.

It is another object of the present invention to provide a device to simultaneously and independently measure two or more gases with negligible or no spectral interference.

It is another object of the present invention to provide a device using an optical switch to simultaneously measure two or more gases for various applications requiring two optical analysis paths.

It is another object of the present invention to perform dual beam spectroscopy such as gas filter correlation radiometry using a single instrument to measure two or more gases in which the difference and sum signals can be obtained from only one detector for each gas wavelength region of interest.

It is another object of the present invention to accomplish simultaneous and independent measurement of two or more gases using a minimum of optical components.

It is another object of the present invention to accomplish simultaneous but not independent measurement of two or more gases using a minimum of optical components.

It is another object of the present invention to sense the total burden of a mixture of two or more gases using a single instrument.

It is another object of the present invention to detect some threshold level of the presence of any one or a combination of several gases using a single instrument.

It is still another object of the present invention to provide a device to simultaneously measure two or more gases of interest and optimize optical balance.

It is still another object of the present invention to provide a device to simultaneously measure two or more gases of interest and optically optimize optical balance.

It is a further object of the present invention to provide a device to simultaneously measure two or more gases of interest and electronically optimize optical balance.

Additional objects and advantages of the present invention are apparent from the specification and drawings which follow.

SUMMARY OF THE INVENTION

The foregoing and additional objects are obtained by modulating a polarized light beam over a broadband of wavelengths between two alternating orthogonal polarization components. One orthogonal polarization component of the polarization modulated beam is directed along a first optical path and the other orthogonal polarization component is directed along a second optical path. At least one optical path contains one or more spectral discrimination means, with each spectral discrimination means having spectral absorption features of one or more gases of interest being measured. The two optical paths then intersect, and one orthogonal component of the intersected components is transmitted and the other orthogonal component is reflected. This forms a combined polarization modulated beam which contains the two orthogonal components in alternate order.

The combined polarization modulated beam is partitioned into one or more smaller spectral regions of interest where one or more gases of interest has an absorption band. The difference in intensity between the two orthogonal polarization components in each partitioned spectral region of interest is then determined as an indication of the spectral emission/absorption of the light beam along the measurement path. The spectral emission/absorption is indicative of the concentration of the one or more gases of interest in the measurement path. More specifically, one embodiment of the present invention is a gas filter correlation radiometer which comprises a polarizer, a polarization modulator, a polarization beam splitter, a beam combiner, wavelength partitioning means and a detection means. The polarizer polarizes light from a light source into a single, e.g., vertically polarized, component which is then rapidly modulated into alternate vertically and horizontally polarized components by the polarization modulator. The polarization modulator may be used in conjunction with an optical waveplate. The polarization modulated beam is then incident on the polarization beam splitter which transmits light of one orthogonal component, e.g., horizontally polarized, and reflects light of a perpendicular component, e.g., vertically polarized. In a GFCR embodiment using two gas cells to measure two gases (hereinafter "two gas/two gas cells embodiment"), the reflected vertically polarized beam passes through a first gas correlation cell containing a first gas of interest, is reflected by a mirror and is then transmitted or reflected through the beam combiner. The transmitted horizontally polarized beam passes through a second gas correlation cell containing a second gas of interest, is reflected by a mirror, and is reflected or transmitted by the beam combiner. The beam combiner recombines the horizontal and vertical components into a single beam in which the polarization is time varying. The combined light energy is then partitioned into wavelength regions corresponding to each gas' absorption band. A first optical bandpass filter transmits radiation centered on one gas band. This radiation is then focused on a first detector. Radiation reflected from the first optical bandpass filter is incident on a second optical bandpass filter. Radiation within the bandpass of the second filter, centered on the absorption band of the second gas, is transmitted and is focused on a second detector. Partitioning may be accomplished in a number of ways including the use of optical filters, gratings and prisms. Provided the first gas does not have absorption features within the spectral region defined by the bandpass filter of the second gas, the first gas correlation cell acts as a vacuum cell for the second gas, and vice versa. In some instances, the first and second gases, e.g., gases that do not chemically interact, may be contained within the same correlation cell. Measurements of both gases are accomplished simultaneously, independently and without interference. Furthermore, optical or electronic means are provided to balance optical intensities between the two optical paths.

Similar configurations are used for measuring three or more gases, including a GFCR embodiment which measures three gases using two gas cells (hereinafter "three gas/two gas cells embodiment") and a GFCR embodiment which measures three gases using three gas cells (hereinafter "three gas/three gas cells" embodiment). The presence of several gases can also be detected simultaneously but not independently, e.g., to sense the total burden of a mixture of two or more gases without needing to know the concentration of each individually or to detect some threshold level of the presence of any one or a combination of several gases.

DETAILED DESCRIPTION OF THE PREFERRED EMBODIMENTS

Figure 1:
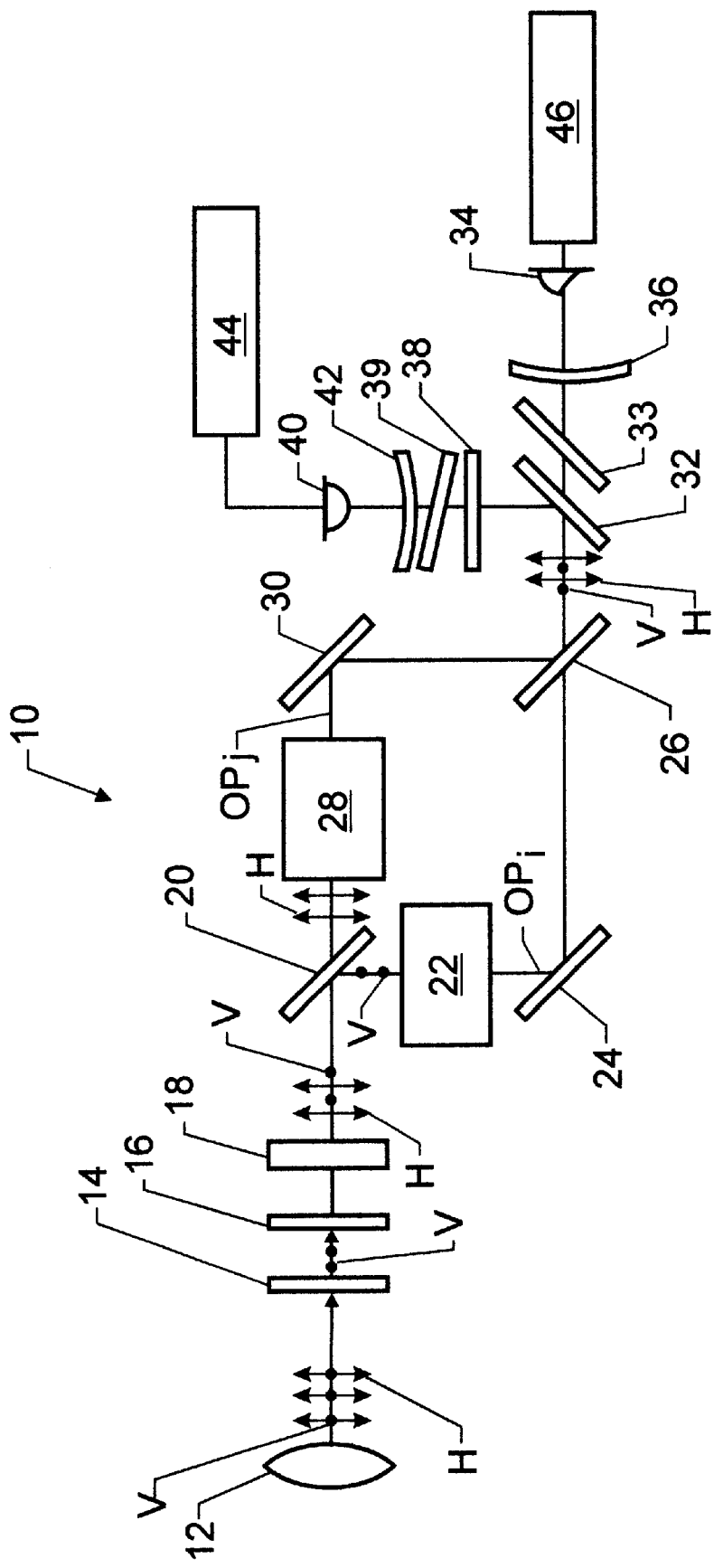
FIG. 1 is a schematic representation of a GFCR configuration for measuring two gases using two gas cells according to the present invention.

Referring now to FIG. 1, a gas filter correlation radiometer (GFCR) 10 is shown according to the present invention. Optics system 12, e.g., a telescope or other lens/mirror system, collects light from a radiation source such as the earth and atmosphere when GFCR 10 is mounted on a satellite or aircraft, a blackbody when GFCR 10 is used as a laboratory or in-situ instrument, the sun, a laser, etc. This light beam, in general, comprises both vertically polarized components V and horizontally polarized components H. Optical polarizer 14 is provided after the optics system 12 and is aligned to polarize the incoming radiation in the desired directional component, e.g., vertically in the embodiment depicted in FIG. 1. A polarization modulator 18 then receives the incident vertically polarized beam and rapidly modulates the output beam between vertical and horizontal polarization. Depending on the measurement application and the type of polarization modulator utilized, the polarization modulation frequency may range from near DC to radio frequencies (RF). The polarization modulator may be used in conjunction with an optical waveplate 16.

Figure 2:
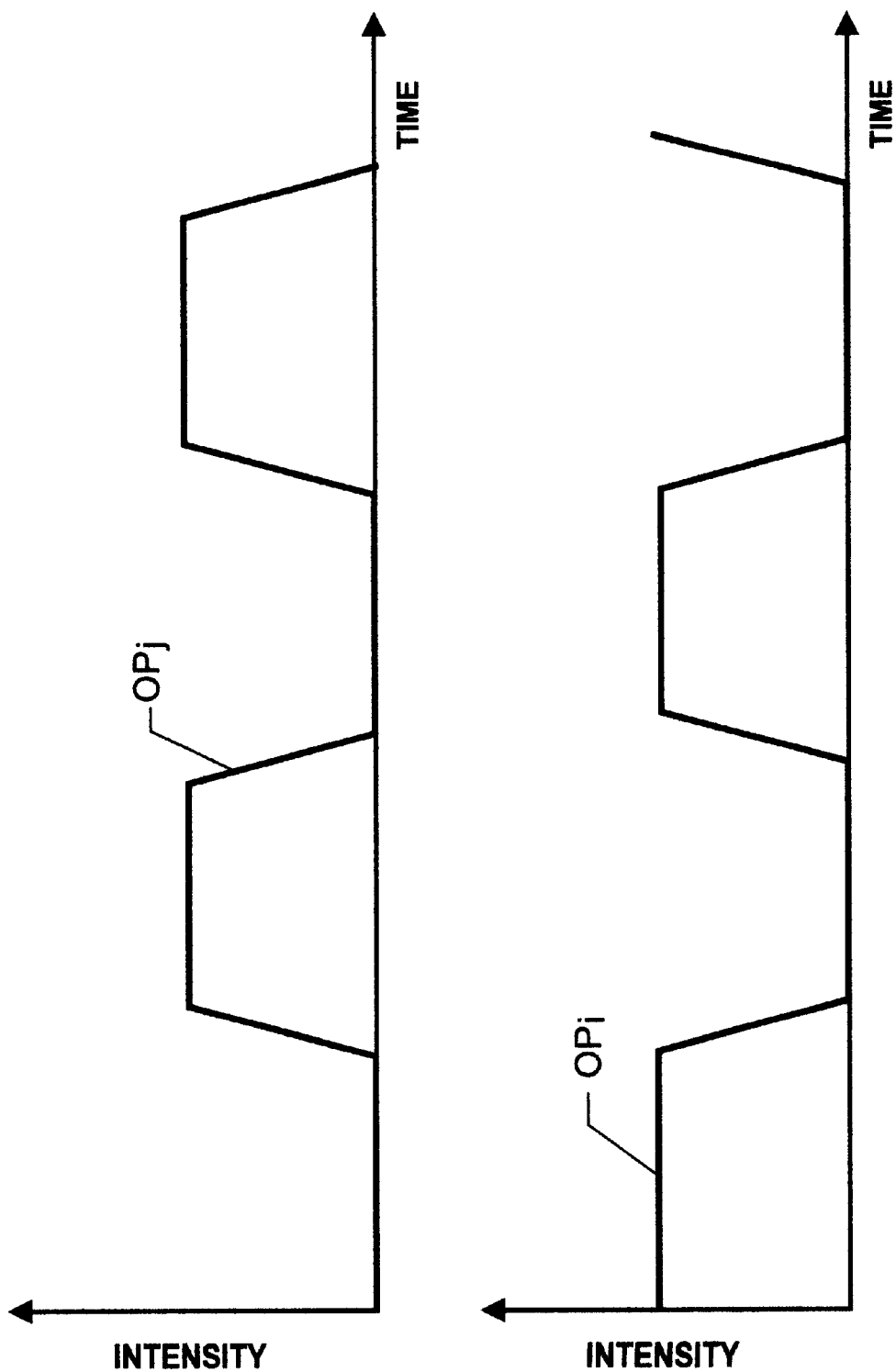
FIG. 2 is a graph showing the approximate change in radiation intensity at some optical wavelength with time along two optical paths generated by the embodiment of FIG. 1.

Polarization beam splitter 20 non-mechanically switches the polarization modulated output beam between two paths by, in the FIG. 1 embodiment, reflecting the beam along path $OP_i$ when it is vertically polarized and transmitting it along path $OP_j$ when it is horizontally polarized. Alternatively, beam splitter 20 may be oriented so as to transmit vertically polarized light and to reflect horizontally polarized light. The approximate temporal change in radiation intensity at a specific optical wavelength for the two optical paths $OP_i$ and $OP_j$ is represented in FIG. 2 as the polarization is switched from vertical to horizontal in the specific embodiment shown in FIG. 1.

Polarization beam splitter 20 thus alternately directs the beam along first and second optical paths. In the specific embodiment shown in FIG. 1, beam splitter 20 is oriented to reflect the vertically polarized light so that it passes through a first gas i correlation cell 22 containing a high optical depth of the first gas i of interest. The exiting light is then reflected by mirror 24 so that it intersects a beam combiner 26. The optical path from the first beam splitter 20 through the first gas i correlation cell 22 to the beam combiner 26 is designated the first gas i correlation optical path $OP_i$.

First beam splitter 20 transmits horizontally polarized light, which then passes through second gas j correlation cell 28 containing a high optical depth of the second gas species j of interest. The exiting light is then reflected by mirror 30 so that it intersects the beam combiner 26. In some instances, the correlation cells 22 and 28 may be replaced by optical interference elements whose spectral transmissions have been designed to approximately replicate the absorption features of the gas species i and j of interest. Such interference elements, however, have disadvantages such as a strong angular dependence and wider spectral notches which allow interference from any spectrally interfering gas species along the measurement path.

The beam combiner 26 may be a second polarization beamsplitter to efficiently combine the two GFCR beams, which represent the two orthogonal polarizations, into a single beam in which the polarization state varies in time at the polarization modulator's 18 fundamental frequency and harmonics of this frequency. Alternately, beam combiner 26 may be a simple broadband beamsplitter, 50/50 as an example. With the 50/50 broadband beamsplitter, the two beams are still combined; however, substantial optical energy is lost. In applications where system performance is not power limited, the second approach would suffice and could save component costs. The optical path from the first beam splitter 20 through the second gas j correlation cell 28 to the beam combiner 26 is designated the second gas j correlation optical path $OP_j$ and should be optically similar, e.g., in length, to the first gas i correlation optical path $OP_i$. This optical similarity is not required but is good optical practice.

The first gas i in the first gas i correlation cell 22 acts optically as a vacuum to the measurement of the second gas j since it is presumed that gas i has negligible absorption features, or optical depth, within the optical bandpass of the gas j measurement. Similarly, the second gas j in the second gas j correlation cell 28 acts as a vacuum to the measurement of the first gas i. Measurements of both gases i and j are accomplished simultaneously, independently and without interference. The two gases i and j must be spectrally non-overlapping within the respective optical bandpasses of the two gas measurements; i.e., the spectral absorption features of gas i must not lie within the measurement optical bandpass of gas j and vice-versa. CO and NO are examples of two such gases.

Beam combiner 26 can be selected to have the same or opposite transmitting and reflecting properties as first beam splitter 20. In the embodiment shown in FIG. 1, it has opposite properties, transmitting the vertically polarized light from the first gas correlation i optical path $OP_i$ and reflecting the horizontally polarized light from the second gas correlation j optical path $OP_j$. The orientation of the mirrors 24 and 30 and the first beam splitter 20 cause the two optical paths to intersect at the beam combiner 26.

After beam combiner 26, a broadband, only limited by the source spectrum and the transmissive and reflective spectral properties of the optical components, of optical wavelengths are present and their respective polarization states are varying in time at the polarization modulator's 18 fundamental and harmonic frequencies; i.e., the beam has rapidly alternating vertical and horizontal components. From this point, optics are used to partition the broadband of optical wavelengths into smaller spectral regions where each of the gases i and j of interest have absorption bands. This partitioning may be accomplished in a number of ways including the use of optical filters, gratings and prisms.

In the embodiment shown in FIG. 1, optical bandpass filter 32 transmits radiation centered on the gas i band. This radiation is then focused by a focusing mirror or refractive lens 36 on first detector 34. This focusing optical element 36 may be eliminated if concentration of the radiation on the detector 34 to achieve higher measurement performance is not necessary. Information regarding the gas i concentration is contained in the detector 34 output at electronic frequencies corresponding to the modulator's 18 fundamental frequency and harmonics and at baseband; i.e., the baseband "DC" signal gives the total power incident on the detector 34 and may be used to normalize the difference signal.

The beam combiner 26 may be oriented in the opposite sense to the first beam splitter 20, wherein the horizontal components pass through and the vertical components reflect to the right, necessitating locating optical bandpass filter 32 below the beam combiner 26 in FIG. 1.

Optical bandpass filter 32 reflects radiation of other wavelengths, but also present in this reflected radiation is a small amount of radiation corresponding to the gas i spectral region. Optical bandpass filter 38 transmits only wavelengths centered about the gas j band and this radiation may be focused by focusing mirror or refractive lens 42 on second detector 40. Again, the electronic output of detector 40 contains gas j concentration information at the polarization modulator's 18 fundamental frequency and harmonics and at baseband.

This partitioning of wavelengths may be accomplished in other ways. One alternative is to substitute a broadband beamsplitter for optical bandpass filter 32. If this is done, however, a bandpass filter must be positioned in front of focusing optics 36 as for bandpass filter 38. Other combinations could include the use of long wave and/or short wave pass filters with bandpass filters. A grating or prism could also be used to separate the various wavelengths.

The DC output (I) of detectors 34 and 40 is proportional to the incident optical intensity within the bandpass of gas species i and j respectively, whereas the amplitude of the AC output at frequencies corresponding to the polarization modulator's 18 fundamental frequency and/or harmonics is related to the difference in intensity ($\Delta$I) between the horizontally and vertically polarized radiation received within the bandpass of gas species i and j. The magnitudes of the difference signal and the average incident intensity signal are related to many factors, including: (1) the radiating properties of the radiation source(s); (2) the concentration and distribution of the gas(es) of interest and any spectrally interfering gas species along the measurement path; (3) pressure and temperature distributions along the measurement path; (4) measurement path length; (5) amount of gas in the correlation cells and the cell length, etc. Radiative transfer algorithms may be used along with information from the $\Delta$I and I signals for each gas of interest to infer total column amounts of the gases of interest along the measurement path. In addition, any other conventional methods may be used to manipulate the data sensed by detectors 34 and 40. For example, an apparatus may be used to calibrate the $\Delta$I/I response of the GFCR for known concentrations of the gases of interest along the measurement path.

Figure 3:
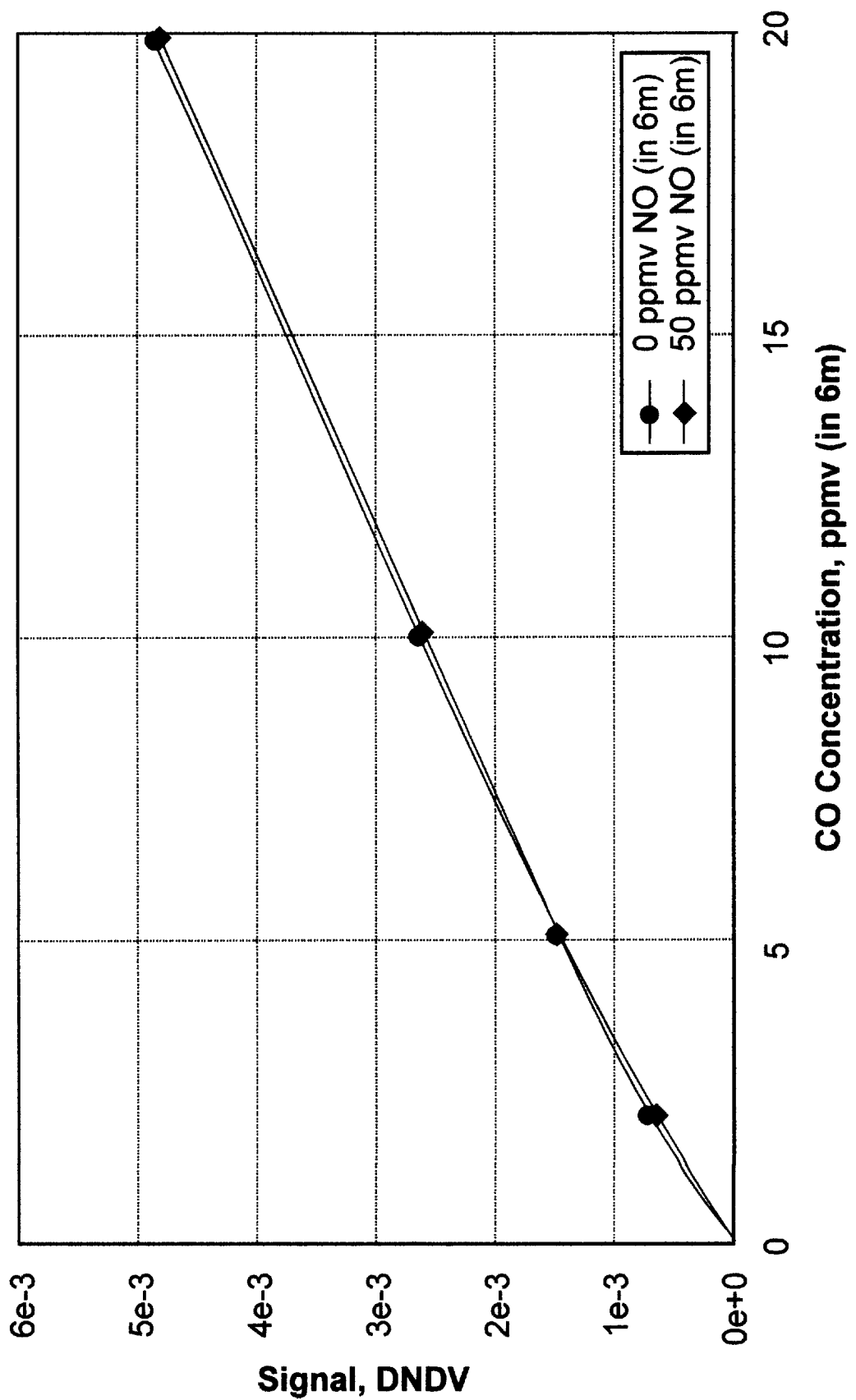
FIG. 3 is a graph showing the effects of NO on GFCR measurement of CO during simultaneous measurements of NO and CO.

One example of a two gas/two gas cell instrument which has been implemented using the FIG. 1 embodiment is a device measuring CO at 4.7 $\mu$m and NO at 5.2 $\mu$m. Results demonstrated no interference to the NO measurement caused by CO, and no interference to the CO measurement caused by NO). FIG. 3 illustrates the lack of interference of NO on a GFCR measurement of CO.

The present invention accordingly allows a single detector to be used for each gas of interest to arrive at the difference $\Delta$I and sum I signals, thereby reducing balancing requirements and detector surface inhomogeneity problems associated with GFCRs that require two detectors to detect a single gas species. The key components of the present invention, as embodied in FIG. 1, are the polarizer 14, polarization beam splitter 16, polarization modulator 18, beam combiner 26, optical bandpass filter 32 and bandpass filter 38. All are commercially available and some basic parameters for use in their selection for various applications are discussed in the following paragraphs. Since many of the component characteristics are wavelength dependent, the spectral region for a desired application is important in component selection.

Polarizer 14 can be eliminated if a polarized light source such as a polarized laser is used. If necessary, the polarizer 14 linearly polarizes the incoming radiation before it is incident on the polarization modulator 18. Important polarizer parameters include extinction ratio, transmission, and angular acceptance. Common polarizer types include prism, reflection, dichroic and wire grid polarizers. Prism and reflection polarizers exhibit high extinction ratios, but their poor angular acceptance may limit their application. Dichroic and wire grid polarizers, on the other hand, possess wide angular acceptance. Dichroic polarizers in addition have high extinction ratios and are commercially available for the visible and near infrared region. Wire grid polarizers exhibit moderate to good extinction ratios and are available for infrared applications.

The purpose of the polarization beam splitter 20 is to separate the orthogonal polarization components of the radiation after the polarization modulator 18. Thus, the loss and extinction ratio for both the transmitted and reflected radiation as well as angular acceptance must be considered. The same consideration must be applied to beam combiner 26 which combines the two orthogonal polarizations in GFCR applications. Dichroic polarizers are not acceptable as beam combiners since they strongly absorb one of the polarization components. Prism and reflection polarization beam splitters may only be used in applications where angular acceptance is not a primary concern. Wire grid polarizers with their large acceptance angle and moderate to good extinction ratios for both transmission and reflection are good beam combiner candidates in the infrared.

The polarization modulator 18, which may also be used in conjunction with a waveplate 16, alternately modulates the state of polarization between two orthogonal linear polarizations, H and V. Important parameters include transmission loss and angular acceptance; and since the modulators are energized devices, energy consumption and heating effects are also important. Electro-optic and photo-elastic modulators are commercially available that operate over a wide spectral region including the UV, visible and infrared. Both modulator types generate a polarization change by modulating the birefringence of an optical crystal. In the electro-optic modulator a strong electric field is applied to yield the desired birefringence change, whereas in the photo-elastic modulator, mechanical stress introduced by a transducer attached to the optical crystal generates the birefringence change. The magnitude of the voltage applied to an electro-optic modulator for a given birefringence modulation increases with increasing optical wavelength. For this reason, modulators using the electro-optic effect are generally more suited for shorter wavelength applications; i.e., UV, visible, and near infrared. An advantage of electro-optic modulators is their wide electronic bandwidth which allows them to be modulated with a variety of electronic waveforms. Square wave or other polarization waveforms can be useful in some GFCR applications to approximate the switching or "chopping" achieved by mechanical switching. To reduce the driving power requirements of photo-elastic modulators, these devices are generally excited at the resonant frequency of the photo-elastic crystal. The photo-elastic modulators must accordingly be excited with a sinusoidal electronic waveform. The resulting polarization modulation will have a quasisine wave characteristic actually containing frequencies corresponding to the polarization modulator's 18 fundamental and harmonic frequencies. Photo-elastic modulators are commercially available for UV, visible and infrared applications. Crystal heating, the mechanical strength of the crystals and the loss of optical transmission are factors limiting longer wavelength applications. Other potential polarization modulators include magneto-optic devices possibly employing the Faraday or Kerr effects, liquid crystal devices (LCDs), etc.

Generally, only a single frequency of detector 34 and 40 $\Delta$I outputs is synchronously demodulated and further processed. Depending on the phase retardation characteristics of the waveplate 16 and the magnitude of the phase retardation of the polarization modulator 18, the optimum frequency to demodulate may be either the fundamental of the polarization modulator 18 or a specific harmonic of the polarization modulator 18.

Figure 4:
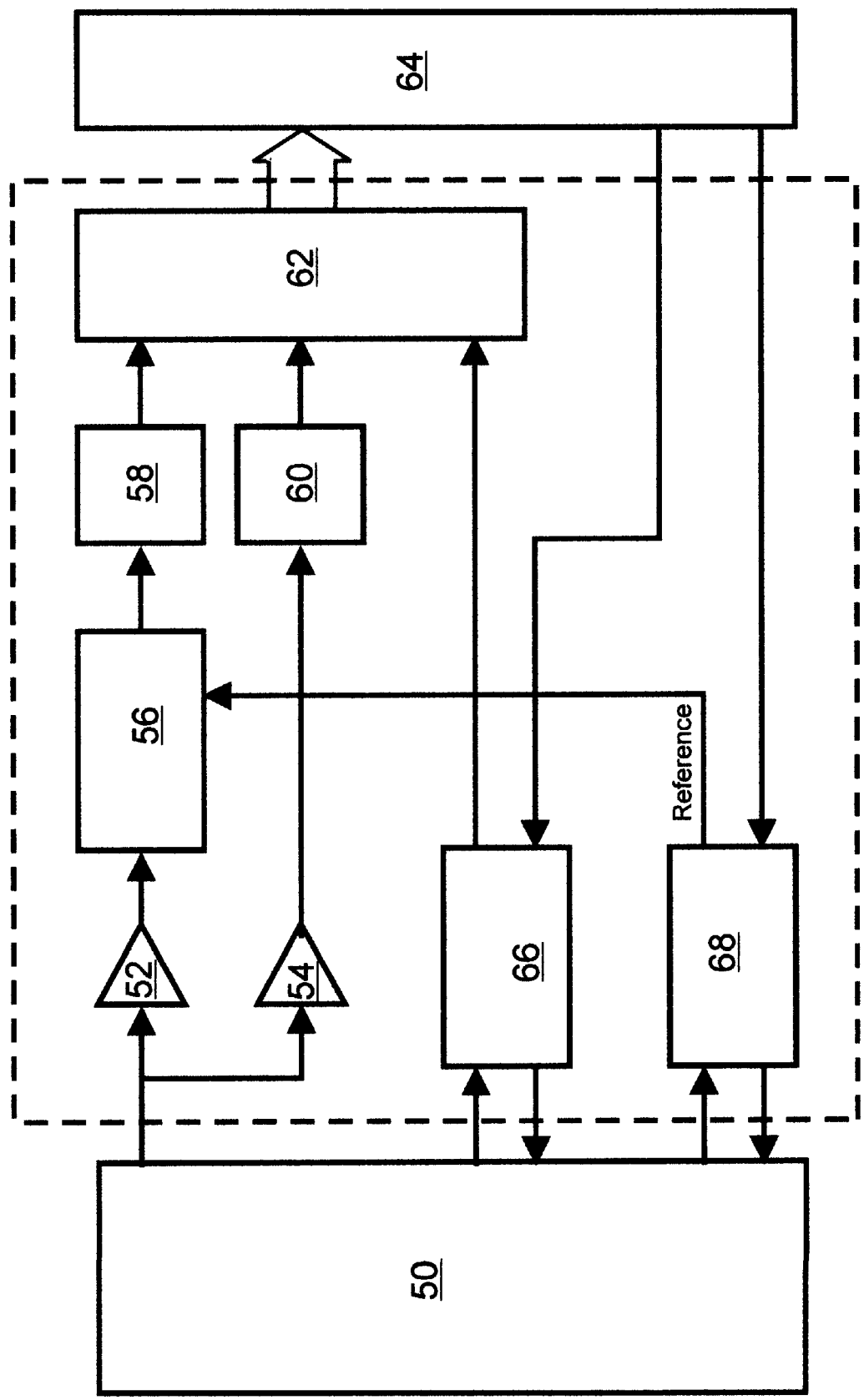
FIG. 4 is a schematic representation of a GFCR configuration data acquisition and control system.
Figure 5:
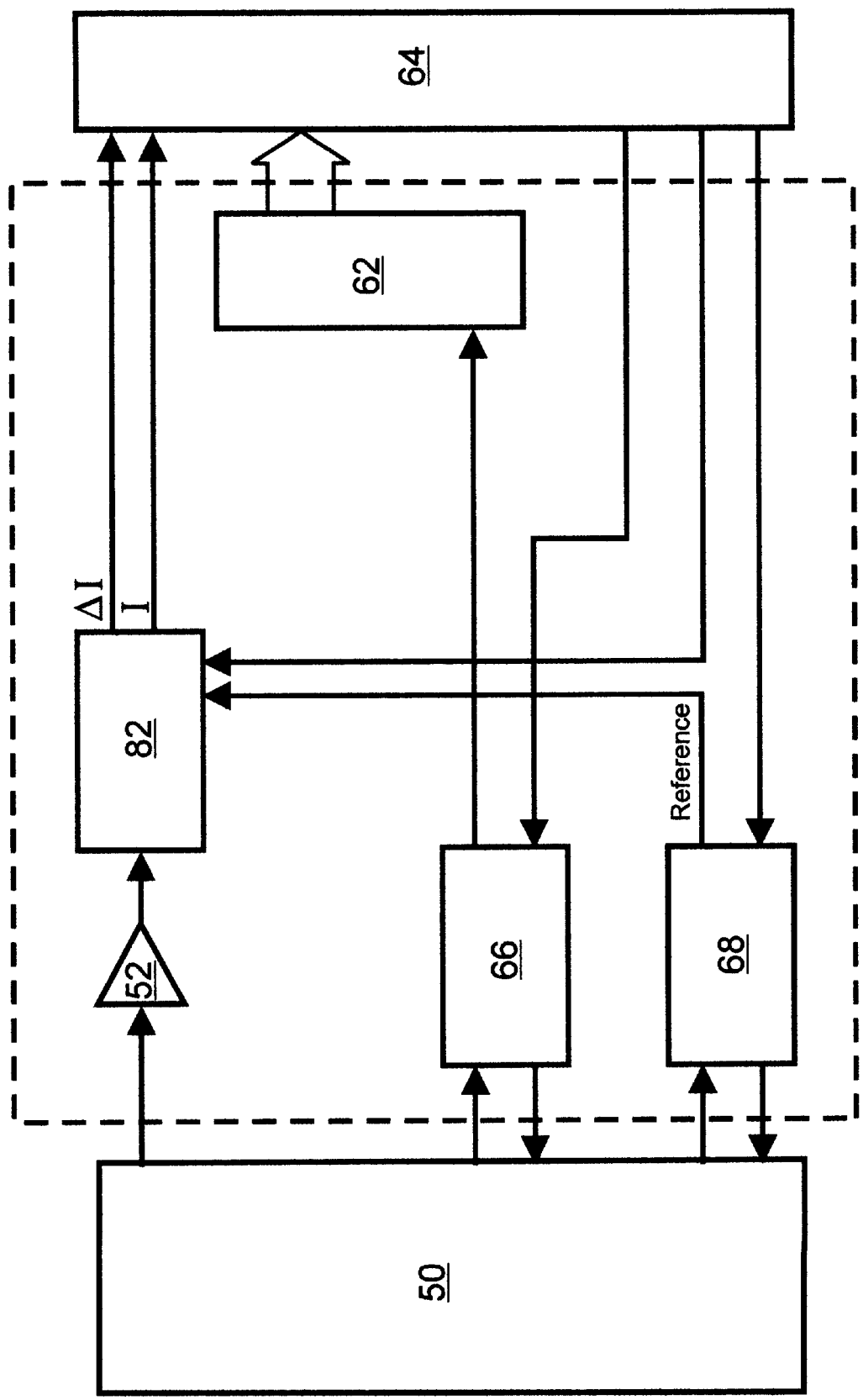
FIG. 5 is a schematic representation of electronic balancing using digital signal processing.

Electronics 44 and 46 control the operation of the GFCR. The operation of the GFCR 50 can be controlled by a PC-based data acquisition and control system such as that shown in the FIG. 4 schematic, which illustrates input from a single detector. The preamplified output of an optical detector is further amplified by two variable gain amplifiers 52 and 54, one for the AC portion of the signal at the modulator's 18 fundamental and/or harmonic frequencies and the other for the DC portion of the signal. A synchronous demodulator 56 extracts the magnitude of the signal at the fundamental and/or harmonic frequencies of the polarization modulator 18 using a frequency reference signal from the polarization modulator 18. The AC and the DC signals are passed through two matched low-pass filters 58 and 60 to narrow the electronic bandpass, thereby suppressing noise. The signals are converted into their digital representations by an A/D converter 62 for processing by a personal computer (PC) 64. Controller 66 controls the operating temperature of the thermoelectrically-cooled detector(s) within the GFCR 50. Controller 68 excites the polarization modulator 18 at some frequency (in the case of a photo-elastic modulator, at its resonant frequency) and at the desired optical phase retardation level, and provides a reference frequency for the synchronous demodulation.

The $\Delta I$ outputs of any of the detectors may be balanced in order to: (1) zero the instrument output (i.e., $\Delta I=0$) independently for each gas, when that gas is not present within the instrument's field of view; or (2) "zero" the instrument output for some background value of a specific gas, e.g., the typical background level of 1800 ppbv $CH_4$. This balance function performed at any one of the detectors, in effect, equalizes the transmission of optical paths $OP_i$ and $OP_j$ within the optical bandpass viewed by that detector. By "balancing" the $\Delta I$ output, certain instrument noises, e.g., systematic radiation source noise and noise associated with fluctuations of the instrument's field of view, may be strongly suppressed, thereby increasing the measurement sensitivity for that particular gas species. In a balanced measurement situation, the same source and misalignment noise is viewed alternately, but rapidly, through both GFCR optical paths and is common mode rejected from the resulting $\Delta I$ signal.

This balance of optical intensities between the two optical paths may be achieved by various means. Examples of such means are: (1) adding a polarization-dependent optic in front of the detectors, and (2) electronic balancing of the detector output which varies the electronics gain synchronously with the passage of the optical beam alternately between the two optical paths. FIG. 1 shows the addition of polarization dependent optics 33 and 39 in front of the detectors 34 and 40, respectively. Each optic 33 and 39 may be a pellicle, e.g., a several micron thick plastic membrane that transmits in the spectral region of interest. The pellicle material, thickness and incident angle may be chosen for optimal path balancing performance. Other optical components might include a thicker infrared transmitting crystal or an amorphous window material. The surfaces of these windows may also be coated with thin films that will enhance their polarization selectivity. An infrared polarizer, e.g., a wire grid polarizer, may also be used to accomplish the optical balance. In this case, the polarizer is rotated to favor one polarization over another. The polarization dependent optics, for simplification purposes, are not shown in FIGS. 9 through 11.

An optical device such as described in the preceding paragraph may be installed and set for a particular balance situation and never reset. However, if nearly perfect balance is required to get maximum sensitivity for a given application, small changes in angle, e.g., of a pellicle, or in rotation, e.g., of the wire grid polarizer, are necessary. This may be accomplished manually by the operator or may be computer controlled through a motorized device.

An alternative technique to achieve balance is through the use of electronic methods. The electronic methods may be used to achieve the entire balance or may be used in conjunction with an optical method to achieve balance. For example, the optical technique may achieve coarse preset balance while the electronic method may be used to fine tune and, through computer control, continually optimize the balance for the measurement task at hand.

Electronic balance may be implemented digitally in the following way. The output V(t) from amplifier 52 is digitized by a digital signal processor (DSP) 82 in FIG. 5. Elements in FIGS. 5 through 8 are numbered consistently with like elements in FIG. 4. This V(t) signal includes the baseband signal as well as the difference signal $\Delta I(t)$ at the polarization modulator's 18 fundamental and harmonic frequencies. In order to zero the difference signal, i.e., $\Delta I=0$, at a specific polarization modulator 18 frequency f, i.e., the fundamental or one of its harmonics, the digitized V(T) signal is, in real time, divided by the balance function $\beta(t)$ where $\beta(t)=1+\alpha \sin(2\pi f t+\phi)$, where the phase $\phi$ is chosen to be in phase with the $\Delta I(t)$ signal at the frequency f and $\alpha$ is adjusted by the computer 64 from time to time to achieve the desired level of balance. The DSP 82 then synchronously demodulates the function $V(t)/\beta(t)$ at frequency f. The demodulated signal is then digitally low pass filtered within the DSP 82 to reduce the electronics bandwidth resulting in greater sensitivity. The magnitude of this demodulated signal is related to the difference in beam intensity $\Delta I$ passing through the optical paths $Op_i$ and $Op_j$. This digital demodulated signal is sent to the computer 64 which in turn may use this information in some programmed way to adjust the value of a in order to optimize the sensor performance. The DSP 82 also averages the $V(t)/\beta(t)$ signal by using a digital low pass filter identical in characteristics to the aforementioned filter. This filter $V(t)/\beta(t)$ function is related to the average power incident on the detector, i.e., the I signal. This digital signal is also transmitted to the computer 64. The computer 64 may then calculate the ratio $\Delta I/I$ which is related to the emission/absorption of the species of interest along the measurement path.

The DSP 82 may also accomplish the balance function by multiplying the signal V(t) by the function $\gamma(t)$ which is simply the inverse of $\beta(t)$. That is, $\gamma(t)=1/\beta(t)$. Thus, $\gamma(t)$ is the geometric progression of $1/\beta(t)$. For small $\alpha$, $\gamma(t) \approx 1-\alpha \sin(2\pi f t+\phi)$.

Figure 6:
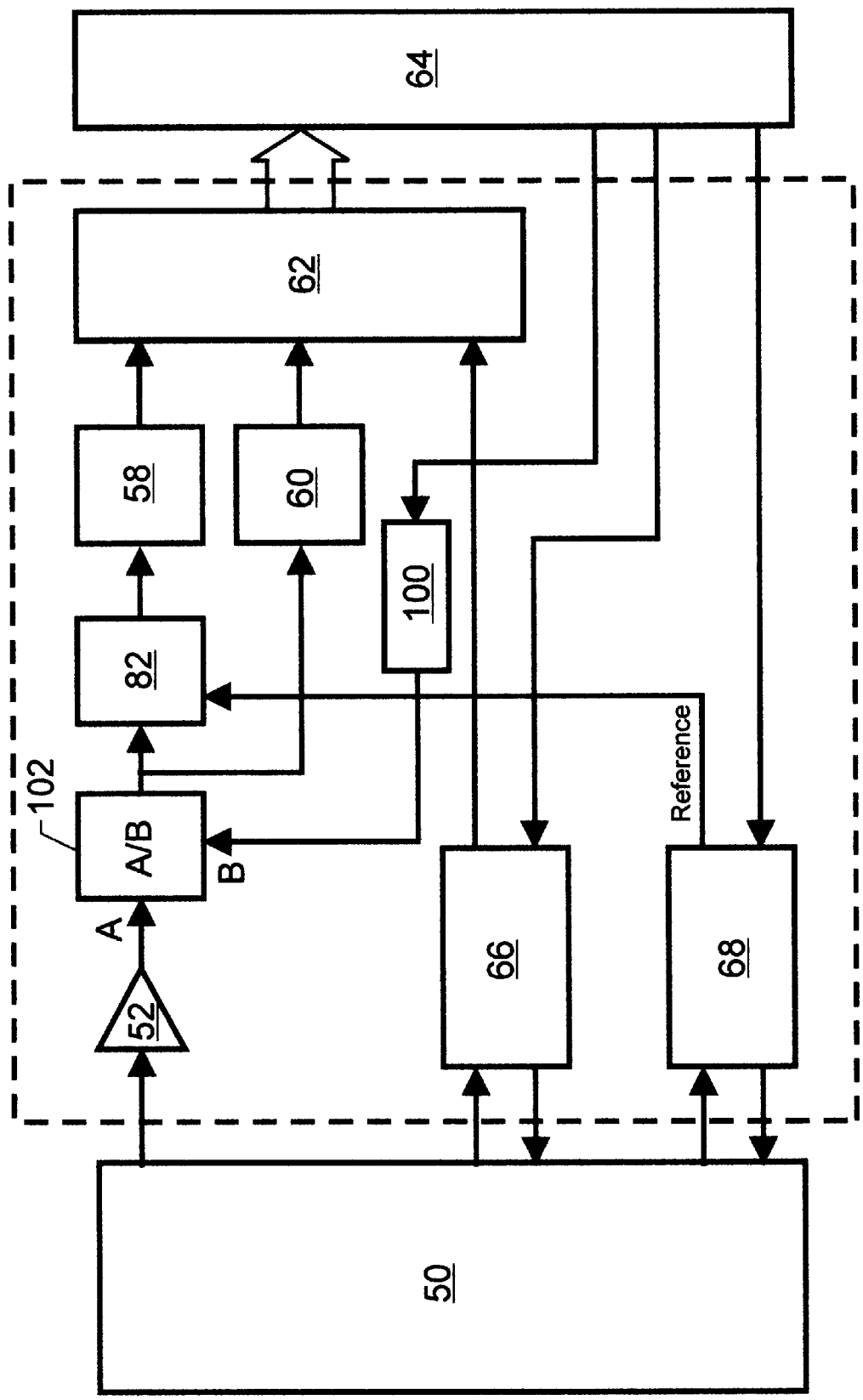
FIG. 6 is a schematic representation of electronic balancing using a gain modulated amplifier.
Figure 7:
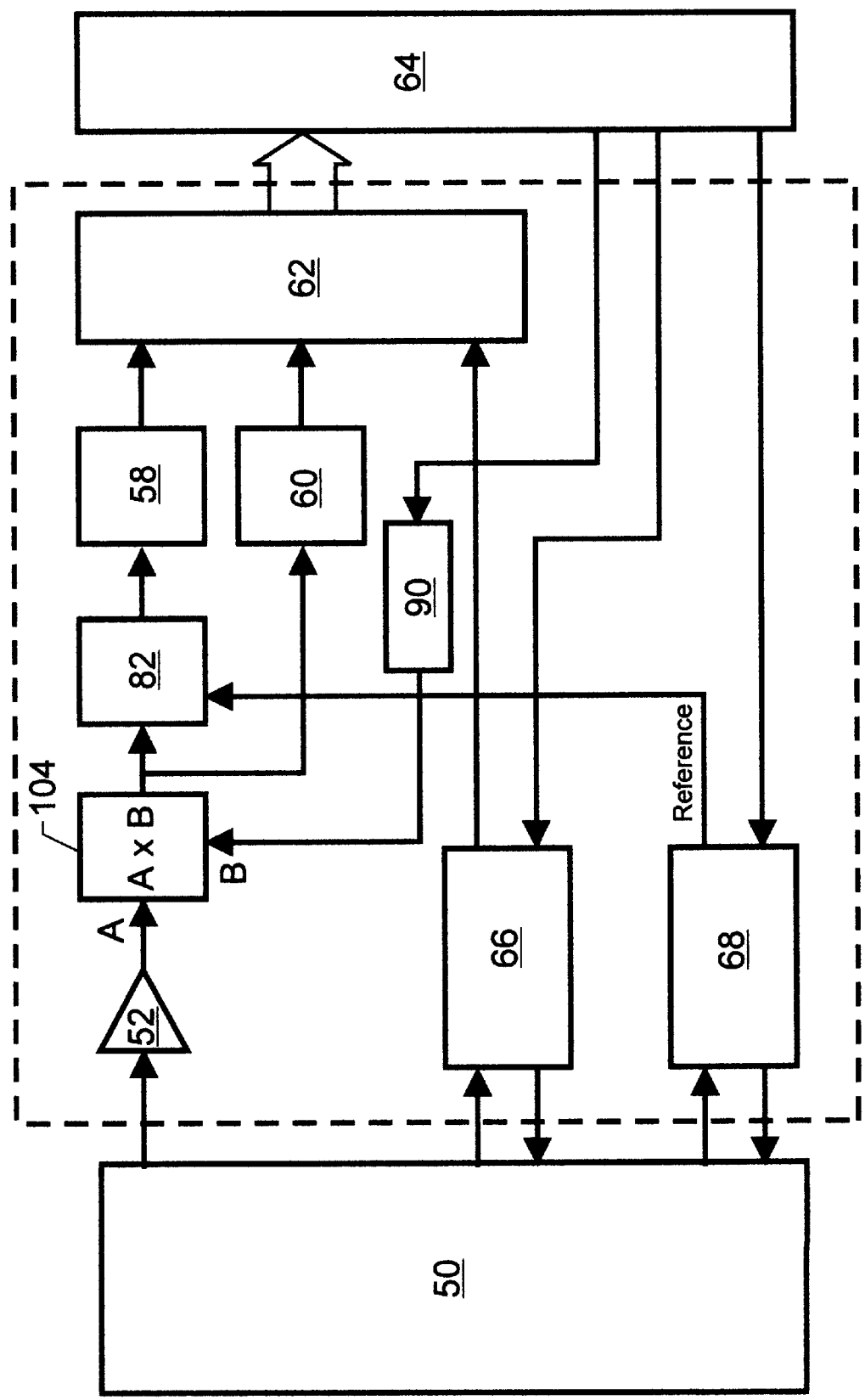
FIG. 7 is a schematic representation of electronic balancing using an analog A/B amplifier.
Figure 8:
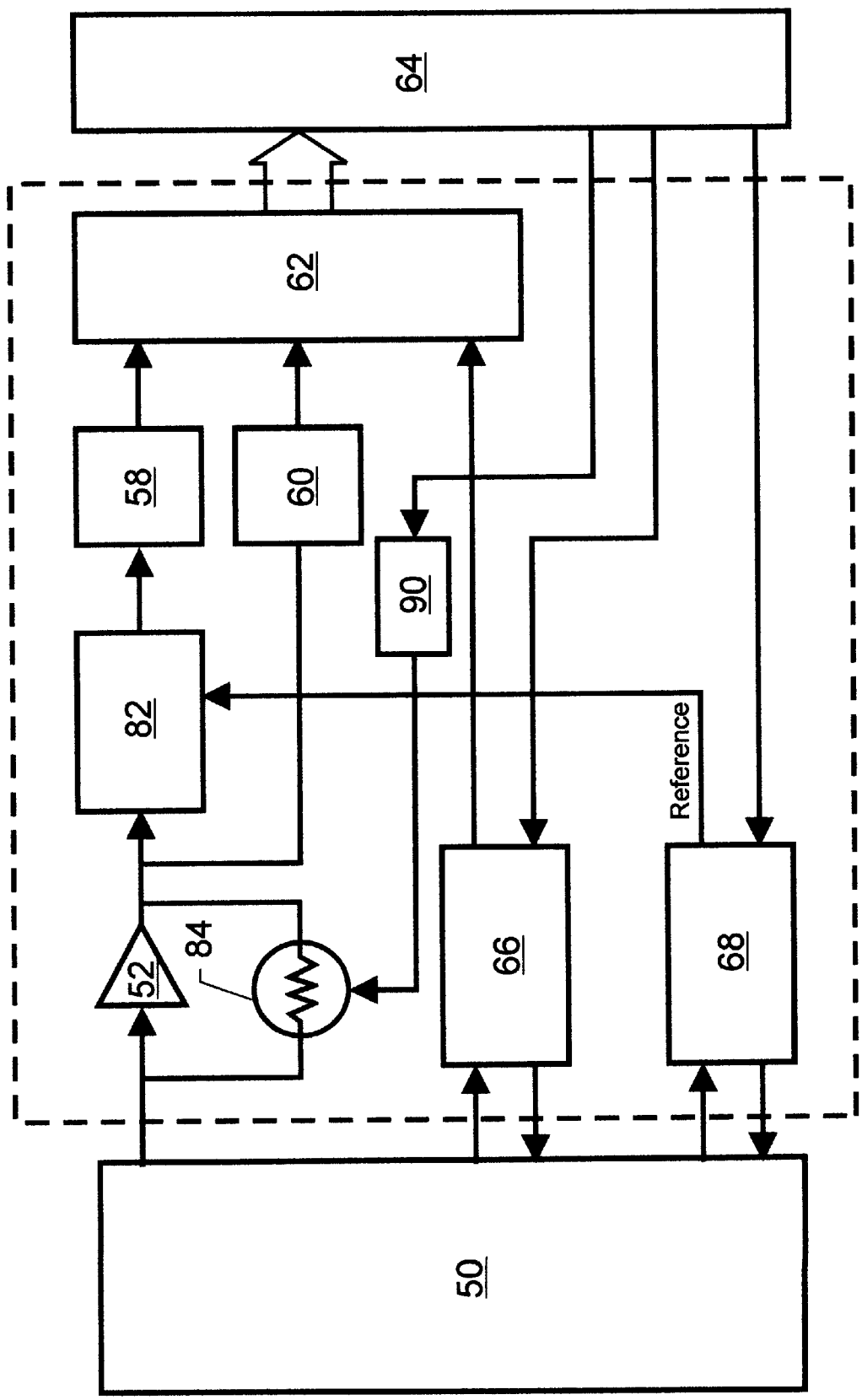
FIG. 8 is a schematic representation of electronic balancing using an analog AXB amplifier.

FIGS. 6 through 8 indicate different ways that electronic balancing may be achieved using analog techniques. For example, in FIG. 6, an A/B amplifier 102 is used where the A input is the analog function V(t) and B is an analog waveform equivalent to $\beta(t)$. Alternately, an AXB amplifier 104 may be used, as shown in FIG. 7, where again A is the analog V(t) signal but B is the analog equivalent of the $\gamma(t)$ signal. In another approach shown in FIG. 8, the gain of detector amplifier 52 is modulated by modulating the resistance of the amplifier's feedback resistor 84. For example, this may be accomplished if the feedback resistor 84 is a photoresistor that is modulated with the analog function $\gamma(t)$. In the analog cases above, additional electronics must be added to generate waveforms that resemble $\beta(t)$ or $\gamma(t)$, i.e., $\gamma(t)$ waveform generator 90 shown in FIGS. 7 and 8, and $\beta(t)$ waveform generator 100 shown in FIG. 6. It is also assumed in the analog cases above that analog synchronous demodulation is used. To change or adjust the balance, the computer 64 must control the magnitude of $\alpha$ in the analog waveform generators 90 and 100.

A drawback of using the polarization-dependent optics is that they must be mechanically tilted or rotated to change or perhaps maintain the balance. However, if used in conjunction with an electronic balancing scheme, the polarization-dependent optics may be preset mechanically for some coarse balance. The electronic balancing circuit may them be used to tweak the balance in some automatic or preprogrammed way. In this way, the highest measurement sensitivity may be consistently achieved.

Figure 9:
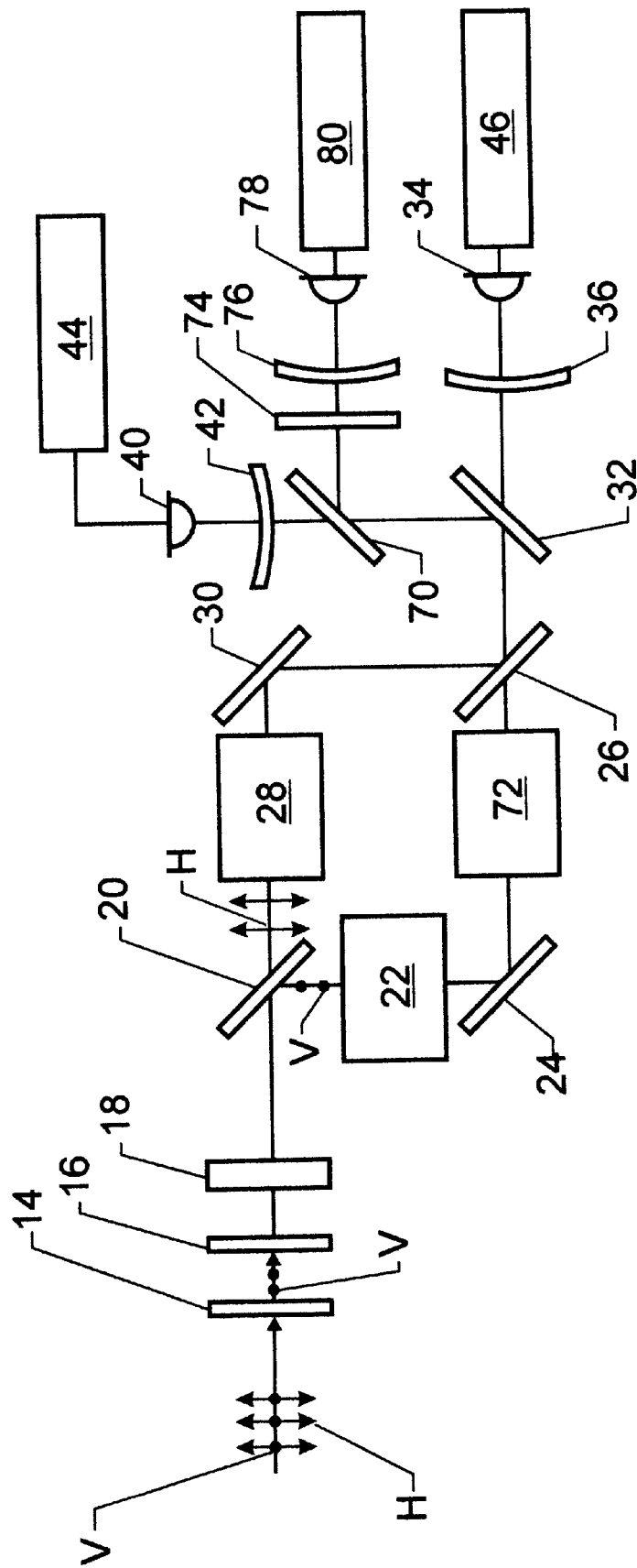
FIG. 9 is a schematic representation of a three gas/three gas cells GFCR embodiment.
Figure 10:
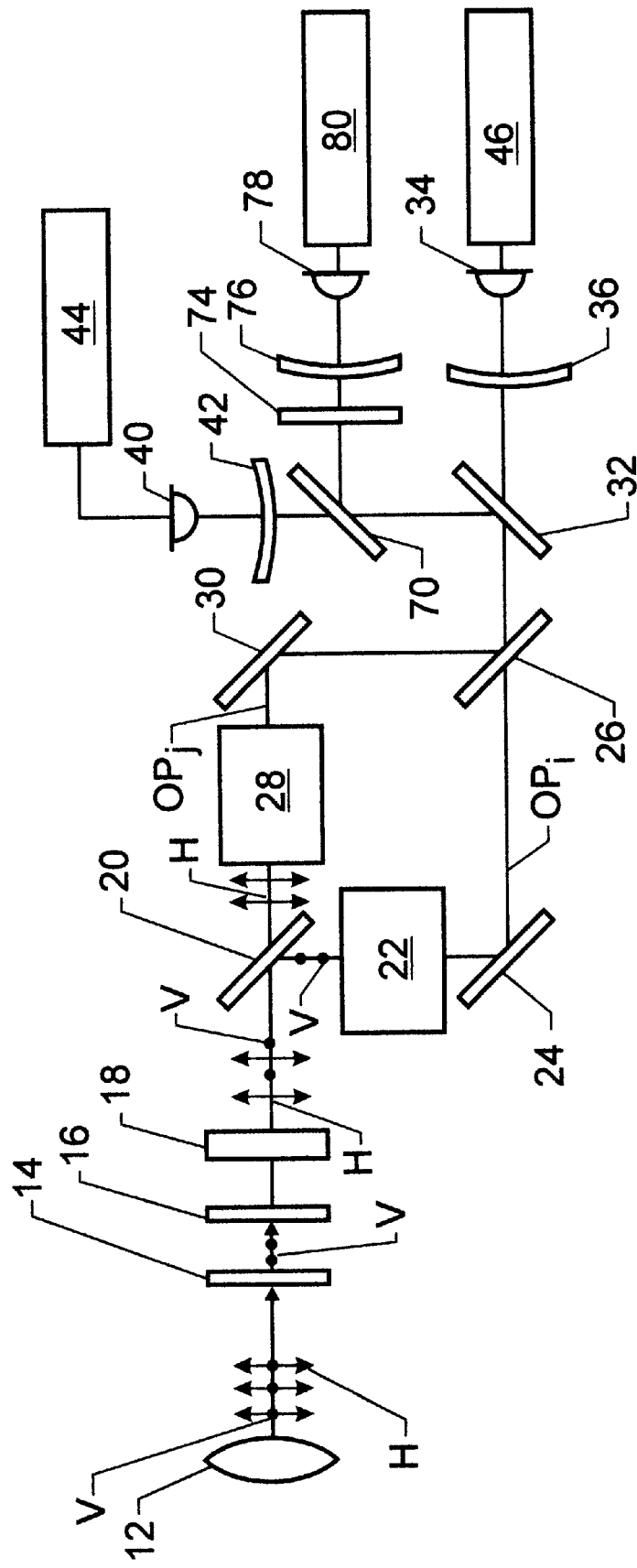
FIG. 10 is a schematic representation of a three gas/two gas cells GFCR embodiment.
Figure 11:
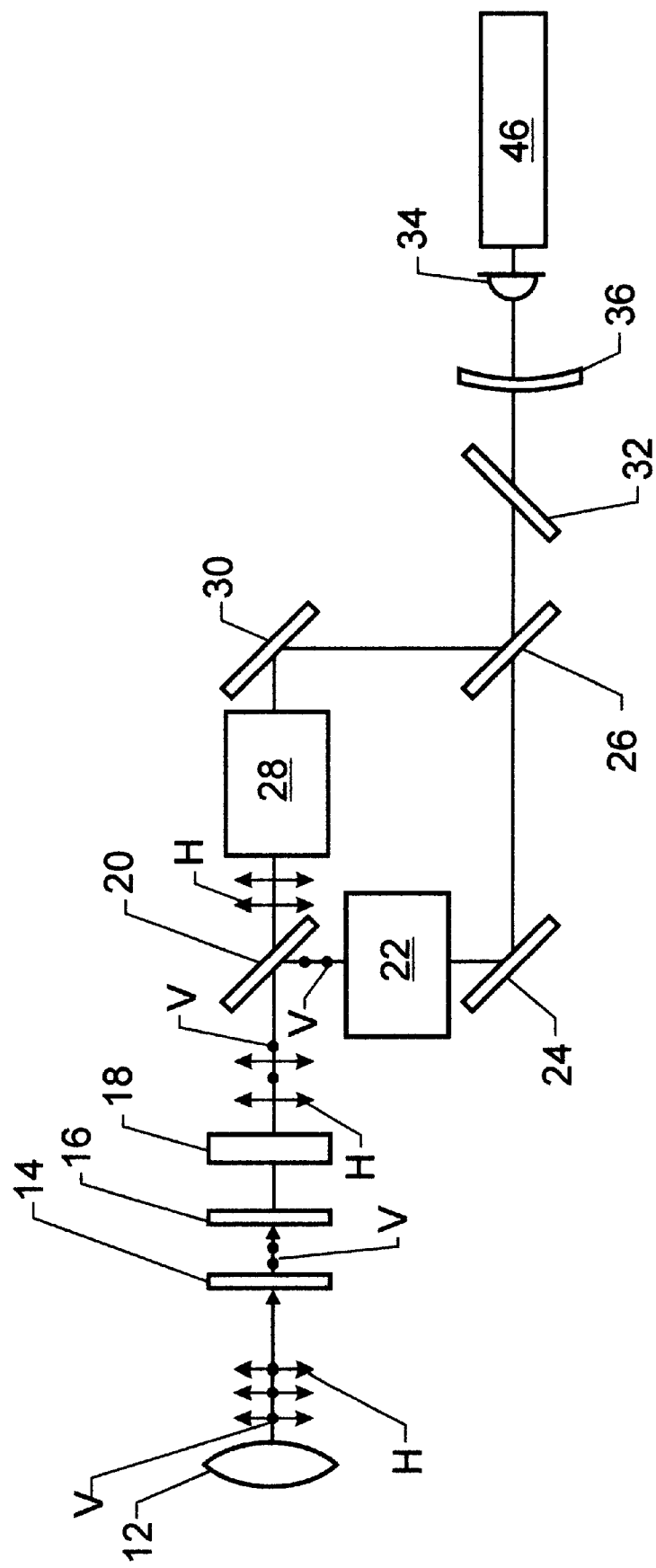
FIG. 11 is a schematic representation of a GFCR configuration for making a total hydrocarbon measurement.

A three gas/three gas cell GFCR embodiment is shown in FIG. 9. Elements in FIGS. 9 through 11 are numbered consistently with like elements in FIG. 1. Like the two gas measurement, the three gases to be measured simultaneously and independently must be spectrally non-overlapping within the various target gas optical bandpasses to ensure that each gas is measured independently with negligible interference. This three gas measurement configuration comprises a second optical bandpass filter 82 and a third set of detection components. Looking more specifically at the three gas embodiment in FIG. 9, the polarization modulated beam is incident on the polarization beam splitter 20 which transmits light of one orthogonal component, e.g., horizontally polarized, and reflects light of a perpendicular component, e.g., vertically polarized. The reflected vertically polarized beam passes through first gas i correlation cell 22 containing a first gas i, is reflected by mirror 24, passes through third gas k correlation cell 72 containing a third gas k, and is then transmitted through beam combiner 26. The transmitted horizontally polarized beam passes through second gas j correlation cell 28 containing a second gas j, is reflected by mirror 30, and is reflected by beam combiner 26. The beam combiner 26 recombines the horizontal and vertical components into a single beam. The first gas i in the first gas i correlation cell 22 acts as a vacuum cell to the measurement of the second gas j and third gas k. Similarly, the second gas j in the second gas j correlation cell 28 acts as a vacuum to the measurement of the first gas i and third gas k, and the third gas k in the third gas k correlation cell 72 acts as a vacuum to the first and second gases i and j. Measurements of gases i, j and k are accomplished simultaneously, independently and with negligible or no interference.

Optical bandpass filter 32 transmits radiation centered on an absorption band of gas i. This radiation is then focused by focusing mirror or refractive lens 36 on first detector 34. Information regarding the gas i concentration is contained in the detector 34 output at frequencies corresponding to the modulator's 18 fundamental frequency and harmonics and at baseband.

Radiation reflected from optical bandpass filter 32 contains a small amount of radiation centered on the gas i band plus all additional wavelengths. Optical bandpass filter 70 then transmits only radiation centered around the gas j band and this beam is subsequently incident on detector 40 after being focused by focusing mirror or refractive lens 42. Again, the electrical output of this detector 40 contains gas j concentration information at the polarization modulator's 18 fundamental frequency and harmonics and at baseband.

Radiation reflected by optical bandpass filter 70 contains a small amount of gas i and gas j band radiation plus all other wavelengths. Bandpass filter 74 transmits only wavelengths centered about the gas k band and this radiation is focused on detector 78 by focusing mirror or refractive lens 76. Again, the output of detector 78 contains gas k concentration information at the polarization modulator's 18 fundamental frequency and harmonics and at baseband.

The previous discussion pertaining to alternate configurations of the FIG. 1 embodiment apply also to this three gas/three gas cells embodiment.

In the three gas/two gas cells embodiment shown in FIG. 10, two gases are contained within the second gas cell 28.

The two gases must be ones that do not react with one another. As an example of such an embodiment, a GFCR measuring the wavelength regions around the 5.2 $\mu$m NO band, the 4.7 $\mu$m CO band, and the 4.4 $\mu$m $C^{13}O_2^{16}$ band is described. Optical bandpass filter 32 transmits radiation centered on the 5.2 $\mu$m band. This radiation is then focused on detector 34. Information regarding the NO concentration is contained in the detector output at frequencies corresponding to the polarization modulator's 18 fundamental frequency and harmonics and at baseband.

Radiation reflected from optical bandpass filter 32 contains a small amount of radiation centered at 5.2 $\mu$m since the optical bandpass filter is not perfect and thus reflects some of this radiation, plus all other additional wavelengths. Optical bandpass filter 70 then transmits only radiation centered around the 4.7 $\mu$m CO band and this beam is subsequently incident on detector 40. Again, the electrical output of this detector contains CO concentration information at the polarization modulator's 18 fundamental frequency and harmonics and at baseband.

Radiation reflected from optical bandpass filter 70 contains some small amount of 5.2 $\mu$m and 4.7 $\mu$m radiation plus all other wavelengths. Bandpass filter 74 transmits only wavelengths centered about the 4.4 $\mu$m $C^{13}O_2^{16}$ band and this radiation is focused on detector 78. Again, the output of detector 40 contains $C^{13}O_2^{16}$ concentration information at the polarization modulator's 18 fundamental frequency and harmonics and at baseband.

The previous discussion pertaining to embodiments one and two apply also to this third embodiment. Four or more gases can be measured simultaneously in like fashion to the embodiments discussed above.

In some applications, it may be important to measure the presence of several gases simultaneously but not independently. Such applications might be (1) to sense the total burden of a mixture of two or more gases without needing to know the concentration of each individually or (2) to detect some threshold level of the presence of any one or a combination of several gases. An example of the first application is the practice of making a "total hydrocarbon" measurement in the exhaust of vehicular traffic, such as automobiles, trucks, etc. Because all hydrocarbons have absorption features in the 3 $\mu$m wavelength region due to rotation-vibration transitions associated with their similar C—H (carbon-hydrogen) bands, conventional measurements, e.g., with interference filters, simply look for absorption changes within this broad spectral region and do not discriminate among the individual hydrocarbon species. Thus, with these conventional techniques, a "total hydrocarbon" measurement results; however, substantial spectral interference to the measurement from other non-hydrocarbon species, e.g, water vapor, may also be present and add uncertainty to the measurement. A GFCR measurement, according to the present invention, may be accomplished by placing two or more of the prominent hydrocarbons expected in vehicular exhaust in a single correlation cell or individually placing the hydrocarbons in a series of cells, or any combination thereof. In such an arrangement, a nearly "total-hydrocarbon" measurement may be made, but with strong suppression of spectral interference from non-hydrocarbon species also absorbing in this region.

FIG. 7 shows such an embodiment. Gas cell 28 contains two or more hydrocarbons. Vacuum cell 22 encloses either a vacuum or a gas or gas mixture exhibiting negligible or no optical depth. Optical bandpass filter 32 transmits radiation centered on the 3 µm wavelength region. This radiation is then focused on detector 34. Information regarding the total hydrocarbon concentration is contained in the detector 34 output at frequencies corresponding to the polarization modulator's 18 fundamental frequency and harmonics and at baseband.

An example of the second application is surveillance of an area to detect some low level (threshold) amount of perhaps one or more toxic gases. Again, it may not be necessary to identify each gas, but, at some limit of detectability, the instrument must provide a warning of the presence of any one or a combination of toxic gases. As in the earlier application, all toxic gases of interest may be contained within one correlation cell or may be individually placed in a series of cells or some combination thereof.

Many modifications, substitutions and improvements will become apparent to one of skill in the art without departing from the spirit and scope of the present invention as described herein and defined in the following claims.

What is claimed is:

1. A method for sensing the concentration of two or more gases of interest within a measurement path, comprising the steps of:
    modulating a polarized light beam, the light beam having passed through the measurement path, over a broadband of wavelengths between two alternating orthogonal polarization components;
    directing one orthogonal polarization component of the polarization modulated beam along a first optical path and directing the other orthogonal polarization component along a second optical path, at least one optical path containing one or more spectral discrimination means, each spectral discrimination means having spectral absorption features of one or more gases of interest;
    intersecting the two optical paths at an intersection point;
    transmitting, at the intersection point, one orthogonal component of the intersected components and reflecting the other orthogonal component, whereby a combined polarization modulated beam is formed comprising the two orthogonal components in alternate order;
    partitioning the combined polarization modulated beam into one or more smaller spectral regions of interest where one or more gases of interest has an absorption band; and
    determining the difference in intensity between the two orthogonal polarization components in each partitioned spectral region of interest as an indication of the spectral emission/absorption of the light beam by the gases of interest in the measurement path, the spectral emission/absorption being indicative of the concentration of the one or more gases of interest in the measurement path.

2. The method of claim 1, further comprising the step of polarizing an unpolarized light beam prior to modulation.

3. The method of claim 1, wherein the one or more spectral discrimination means are one or more gas cells, each gas cell containing one or more gases of interest.

4. The method of claim 1, wherein the one or more spectral discrimination means are one or more optical interference elements, each optical interference element having spectral transmissions which approximately replicate the absorption features of one or more gases of interest.

5. The method of claim 1, further comprising the step of balancing the optical intensities between the two optical paths for one or more partitioned spectral regions of interest.

6. The method of claim 5, wherein the balancing is performed optically within the corresponding partitioned spectral region of interest.

7. The method of claim 5, wherein the balancing is performed electronically.

8. A multi-gas sensor for simultaneously measuring the concentration of two or more gases of interest within a measurement path, comprising:
    a polarization modulator for modulating a polarized light beam, the light beam having passed through the measurement path, over a broadband of wavelengths between two alternating orthogonal polarization components;
    a polarization beam splitter for switching the polarization modulated beam by transmitting one orthogonal polarization component of the polarization modulated light beam along a first optical path and reflecting the other orthogonal polarization component of the polarization modulated light beam along a second optical path;
    at least one spectral discrimination means located in at least one of the first and second optical paths, each spectral discrimination means having spectral absorption features of one or more gases of interest;
    means for intersecting the two optical paths at an intersection point;
    a beam combiner located at the intersection point of the first and second optical paths, the beam combiner transmitting one orthogonal component of the intersected components and reflecting the other orthogonal component, whereby a combined polarization modulated beam is formed comprising the two orthogonal components in alternate order;
    means for partitioning the combined polarization modulated beam into a detection path for each wavelength region of interest corresponding to an absorption band for the gases of interest;
    a detector in each detection path for receiving the incident partitioned beam in the corresponding wavelength region of interest and for sensing a difference in the intensity between the two orthogonal polarization components of the incident partitioned beam as an indication of the spectral emission/absorption of the light beam by the gases of interest in the measurement path, the spectral emission/absorption being indicative of the concentration of the one or more gases of interest in the measurement path; and
    a control and data acquisition means for exciting the polarization modulator, controlling the temperature of each detector, and processing the output of each detector.

9. The multi-gas sensor of claim 8, wherein each spectral discrimination means comprises a gas correlation cell, each gas correlation cell containing at least one gas of interest.

10. The multi-gas sensor of claim 8, wherein each spectral discrimination means comprises an optical interference element having a spectral transmission which approximately replicates the absorption feature of a wavelength region of interest.

11. The multi-gas sensor according to claim 8, further comprising an optical polarizer for polarizing an incoming light beam prior to modulation by the polarization modulator.

12. The multi-gas sensor according to claim 8, further comprising an optical waveplate positioned before the polarization modulator.

13. The multi-gas sensor according to claim 8, wherein the polarization modulator is selected from the group consisting of electro-optic, magneto-optic and photo-elastic modulators and liquid crystal devices.

14. The multi-gas sensor according to claim 8, wherein the polarization beam splitter is selected from the group consisting of prism, reflector, and wire grid beam splitters.

15. The multi-gas sensor according to claim 8, wherein the intersecting means comprises a respective reflecting mirror arranged in each of the two optical paths.

16. The multi-gas sensor according to claim 8, wherein the intersecting means is located such that the two optical paths from the polarization beam splitter to the intersection point are optically similar.

17. The multi-gas sensor according to claim 8, wherein the beam combiner is selected from the group consisting of polarization beamsplitter and broadband beamsplitter.

18. The multi-gas sensor according to claim 8, wherein the partitioning means comprises one or more optical filters operatively arranged to pass a unique wavelength band to each detector, each unique wavelength band corresponding to an absorption band of one or more gases of interest.

19. The multi-gas sensor according to claim 18, further comprising a focusing means positioned in front of each detector for focusing the incident beam on each detector, wherein the focusing means is selected from the group consisting of focusing mirror and refractive lens.

20. The multi-gas sensor according to claim 8, wherein the partitioning means comprises a beamsplitter and one or more downstream optical filters, the beamsplitter and optical filters operatively arranged to pass a unique wavelength band to each detector, each unique wavelength band corresponding to an absorption band of one or more gases of interest.

21. The multi-gas sensor according to claim 19, further comprising a focusing means in each detection path for focusing the incident beam on each detector, wherein the focusing means is selected from the group consisting of focusing mirror and refractive lens.

22. The multi-gas sensor according to claim 8, wherein two or more gases of interest have absorption features in a common wavelength region and are measured simultaneously but not independently.

23. The multi-gas sensor according to claim 8, wherein the gases of interest are spectrally non-overlapping within the one or more wavelength regions of interest and are measured simultaneously and independently.

24. The multi-gas sensor according to claim 8, wherein the optical polarizer is selected from the group consisting of prism, reflection, dichroic and wire grid polarizers.

25. The multi-gas sensor according to claim 8, further comprising a vacuum cell located in one of the first and second optical paths.

26. The multi-gas sensor of claim 8, wherein the control and data acquisition means comprises:
   a variable gain amplifier corresponding to each detector for amplifying the AC portion of the detector's signal;
   a variable gain amplifier corresponding to each detector for amplifying the DC portion of the detector's signal;
   a synchronous demodulator corresponding to each detector for receiving the amplified AC signal and extracting its magnitude using a frequency reference signal from the polarization modulator;
   a low pass filter corresponding to each detector for receiving the amplified DC signal and narrowing its electronic bandpass;
   a low pass filter corresponding to each detector for receiving the demodulated AC signal and narrowing its electronic bandpass;
   an A/D converter for converting the filtered AC and DC signals into digital representations for processing by a computer;
   a controller corresponding to each detector for controlling the operating temperature of the corresponding detector; and
   a controller for exciting the polarization modulator and providing a reference frequency for the demodulator.

27. The multi-gas sensor of claim 8, further comprising a polarization dependent optic operatively positioned in front of at least one detector to balance the corresponding optical intensities between the two optical paths.

28. The multi-gas sensor of claim 27, wherein the polarization dependent optic is selected from the group consisting of pellicle, infrared transmitting crystal, amorphous window and infrared polarizer.

29. The multi-gas sensor of claim 8, wherein the control and data acquisition means balances the optical intensities between the two optical paths for one or more partitioned spectral regions of interest.

* * * * *

UNITED STATES PATENT AND TRADEMARK OFFICE
CERTIFICATE OF CORRECTION

PATENT NO. : 6,008,928
DATED : December 28, 1999
INVENTOR(S) : Glen W. Sachse,

It is certified that error appears in the above-identified patent and that said Letters Patent is hereby corrected as shown below:

[75] Inventors: Glen W. Sachse
Liang-guo Wang
Peter J. LeBel
Tommy C. Steele
Mauro Rana Signed and Sealed this Seventeenth Day of April, 2001

Attest:

NICHOLAS P. GODICI

Attesting Officer     Acting Director of the United States Patent and Trademark Office